United States Patent [19]

Koch et al.

[11] Patent Number: 5,384,606
[45] Date of Patent: Jan. 24, 1995

[54] DIFFRACTIVE/REFRACTIVE SPECTACLE AND INTRAOCULAR LENS SYSTEM FOR AGE-RELATED MACULAR DEGENERATION

[75] Inventors: Donald G. Koch, Burbank; Albert C. Ting, Laguna Niguel; Jim-Son Chou, Irvine, all of Calif.

[73] Assignee: Allergan, Inc., Irvine, Calif.

[21] Appl. No.: 901,932

[22] Filed: Jun. 22, 1992

[51] Int. Cl.$^6$ .................. G02C 7/02; G02C 7/08; A61F 2/16
[52] U.S. Cl. .................. 351/158; 351/159; 351/177; 623/6
[58] Field of Search .................. 351/158, 159, 160 R, 351/160 H, 161, 162, 177; 623/6

[56] References Cited

U.S. PATENT DOCUMENTS

| | | | |
|---|---|---|---|
| 4,010,496 | 3/1977 | Neefe | 351/161 |
| 4,504,982 | 3/1985 | Burk | 623/6 |
| 4,655,565 | 4/1987 | Freeman | 351/161 |
| 4,666,446 | 5/1987 | Koziol et al. | 623/6 |
| 4,710,197 | 12/1987 | Donn et al. | 351/160 R |
| 4,828,558 | 5/1989 | Kelman | 351/161 |
| 4,863,468 | 9/1989 | Feinbloom et al. | 623/6 |
| 4,957,506 | 9/1990 | Mercier | 623/6 |
| 5,030,231 | 7/1991 | Portney | 623/6 |
| 5,044,706 | 9/1991 | Chen | 359/565 |
| 5,074,875 | 12/1991 | Donn et al. | 351/160R |

FOREIGN PATENT DOCUMENTS

| | | |
|---|---|---|
| 9169227 | 11/1991 | Australia . |
| 2040579 | 10/1991 | Canada . |
| 0157476 | 10/1985 | European Pat. Off. . |
| 0359179 | 3/1990 | European Pat. Off. . |
| 0441206 | 8/1991 | European Pat. Off. . |
| 0461856 | 12/1991 | European Pat. Off. . |

OTHER PUBLICATIONS

Faklis, D. & Morris, G., "Diffractive Lenses in Broadband Optical System Design", *Photonics Spectra*, 25(12)131–134, Dec. 1991.

Faklis, D. & Morris, G., "Optical Design With Diffractive Lenses", *Photonics Spectra*, 25(11) 205–208, Nov. 1991.

Swanson, G. J., "Binary Optics Technology: Theoretical Limits on the Diffraction Efficiency of Multilever Diffractive Optical Elements", *Technical Report* 914, Lincoln Laboratory, MIT, Mar. 1, 1991.

Forrest, Gary T., "Diffractive optics finds applications", *Laser Focus World*, p. 45 Feb. 1991.

Farn, M. W. & Goodman, J. W., "Effect of vlsi fabrication errors on kinoform efficiency", SPIE vol. 1211, pp. 125–136, 1990.

Cox, J. A., Werner, T., Lee, J., Nelson, S., Fritz, B., Bergstrom, J., "Diffraction efficiency of binary optical elements", *SPIE* vol. 1211, pp. 116–124, 1990.

Swanson, G. J., "Binary Optics Technology: The Theory and Design of Multi-level Diffractive Optical Elements", *Technical Report* 854, Lincoln Laboratory MIT Aug. 14, 1989.

Buralli, D. A., Morris, G. M., Rogers, J. R., "Optical performance of holographic kinoforms", *Applied Optics*, 28(5) 976–983, Mar. 1, 1989.

Riedl, M. J., "Predesign of Diamond Turned Refractive/Diffractive Elements for IR Objectives", handout at SPIE Conference Jan. 22, 1992.

Primary Examiner—Scott J. Sugarman
Attorney, Agent, or Firm—Gordon L. Peterson

[57] ABSTRACT

An ophthalmic lens system (11), including an IOL (15) having a negative IOL lens portion (22) and a positive lens (13) adapted to be outside the eye and direct light toward the negative IOL lens portion. At least one of the surfaces of at least one of the lenses has a diffractive portion.

23 Claims, 2 Drawing Sheets

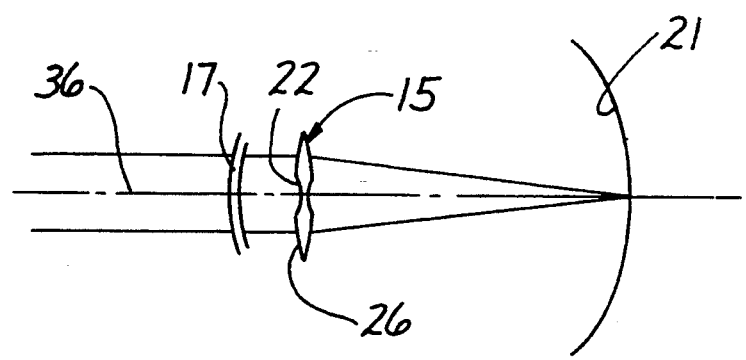
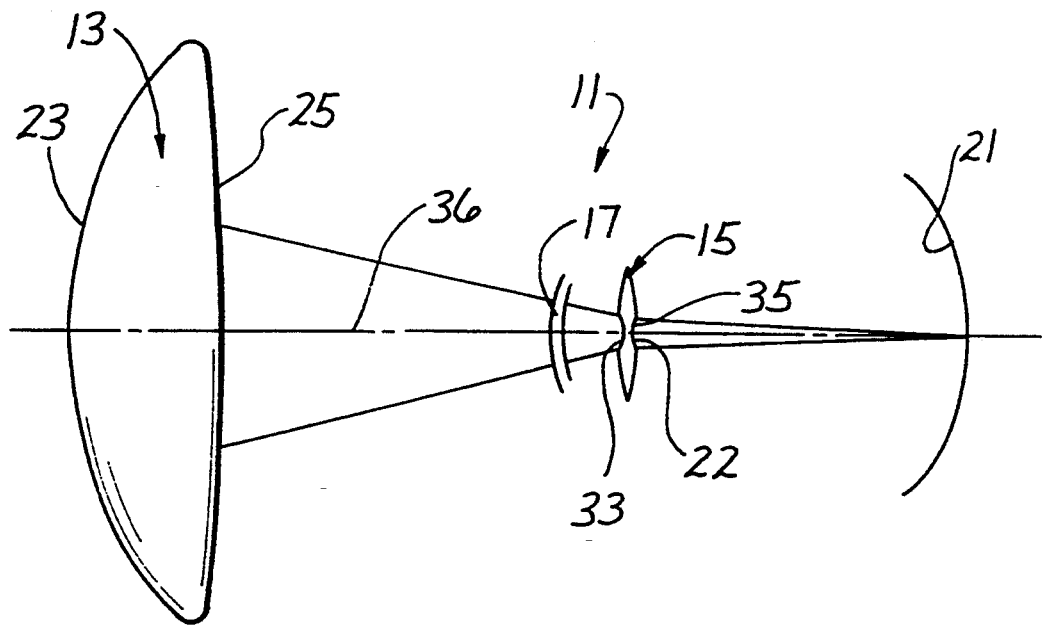
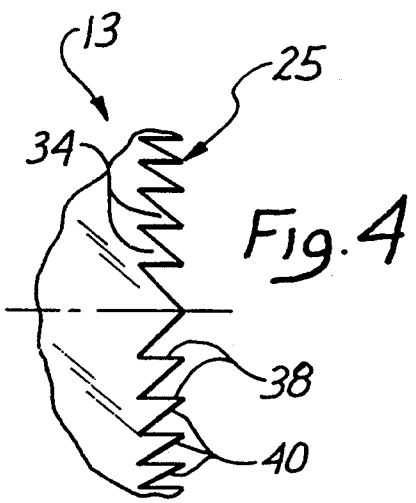
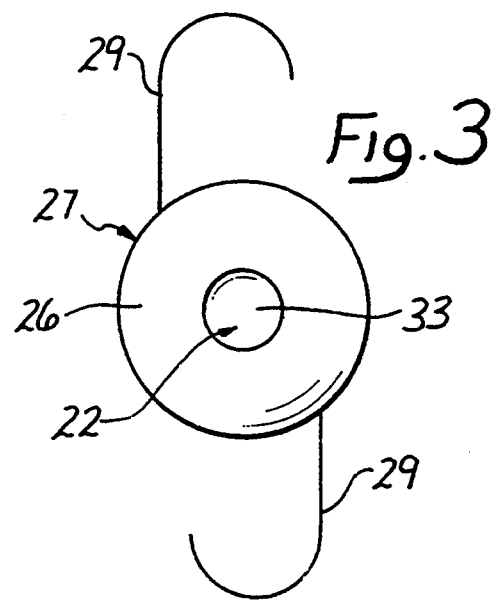

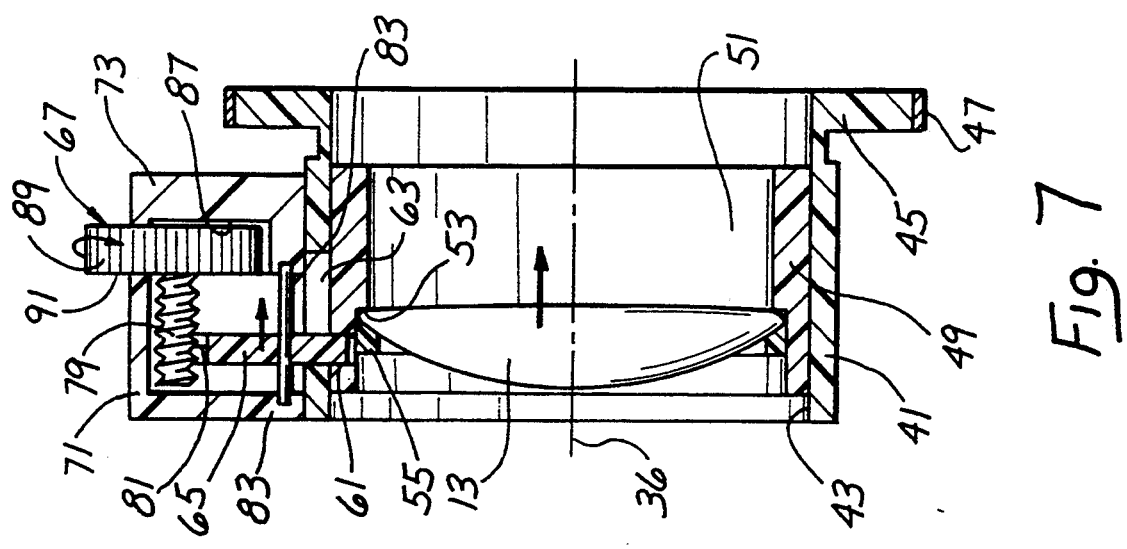
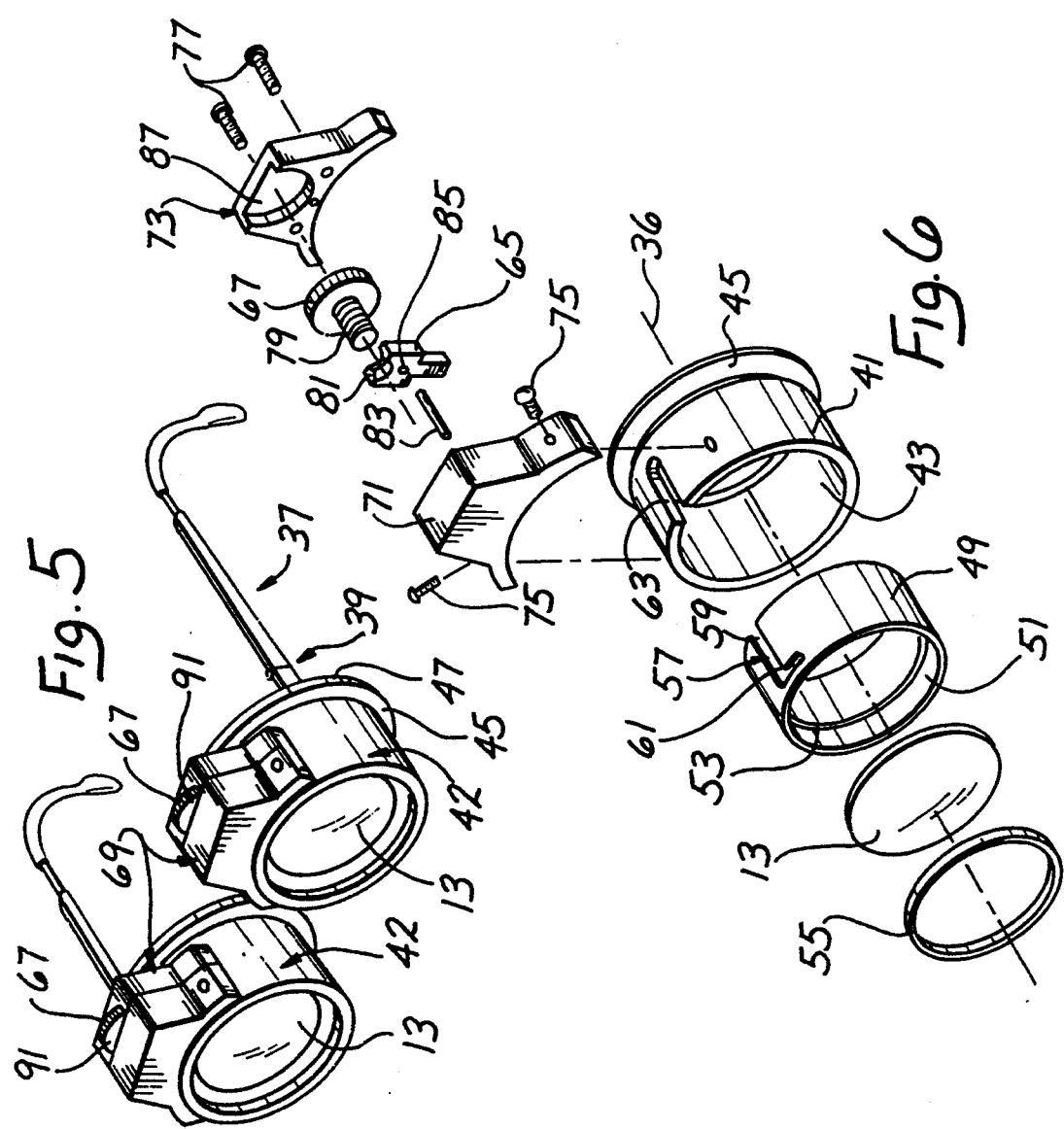

DIFFRACTIVE/REFRACTIVE SPECTACLE AND INTRAOCULAR LENS SYSTEM FOR AGE-RELATED MACULAR DEGENERATION

FIELD OF THE INVENTION

This invention relates to an ophthalmic lens system and more particularly to an ophthalmic lens system for use by patients having a condition known as macular degeneration.

BACKGROUND OF THE INVENTION

Macular degeneration, which is generally agerelated, affects a central region of the retina known as the macula. Macular degeneration can lead to a gradual or rapid loss of vision to the level of 20/200 or less. It may affect, for example, only about ¼ to 4 square millimeters of the macula, thereby leaving 95 to 99 percent of the retina unaffected. Accordingly, central vision, such as for reading and watching television, can be lost while peripheral vision remains relatively intact.

Vision problems for the patient are compounded if macular degeneration is also accompanied by cataracts on the natural lens of the affected individual. One way of dealing with this compounded vision problem is disclosed in Donn et al U.S. Pat. No. 4,710,197. The disclosed approach is to replace the cataractic natural lens of the eye with a negative intraocular lens and to employ a single, positive lens element on a spectacle frame in combination with the intraocular lens (IOL). A positive or negative contact lens may also be used in this system to further correct the patient's vision.

Another approach is disclosed in Portney U.S. Pat. No. 5,030,231. This patent discloses an IOL with a negative IOL portion and bi-element spectacles serving as a positive lens to direct light toward the negative lens portion of the IOL.

It is often desirable to minimize the vertex distance, i.e., the spacing between the outer surface of the eye and the spectacle lens. A large vertex distance reduces the field of fixation, i.e., the maximum angle within which the eye can move and still see an object clearly and tends to make the spectacles less comfortable to wear and not aesthetically pleasing. A large vertex distance also tends to draw attention to the visual handicap of the wearer. A telephoto lens system as described in U.S. application Ser. No. 730,471 filed on Jul. 16, 1991, now U.S. Pat. No. 5,196,028 can be used to reduce the vertex distance.

SUMMARY OF THE INVENTION

This invention provides a number of important improvements in an ophthalmic lens system of the type usable to assist a patient with central retinal vision problems of which macular degeneration is one example. These features may be employed individually or in combination.

This invention is applicable to an ophthalmic lens system which includes an IOL adapted for implantation in the eye and having a negative IOL lens portion, and a positive lens system adapted to be outside the eye and direct light toward the negative IOL portion of the IOL. Each of the IOL lens portion and the positive lens system has a plurality of lens surfaces.

One important feature of this invention is that at least one of the lens surfaces includes a diffractive portion. The diffractive portion may comprise all or a portion of the lens surface. The diffractive portion may, for example, correct in whole or in part for chromatic aberrations. The diffractive portion is especially adapted to accomplish this because the chromatic dispersion of a diffractive surface is opposite that of a refractive surface for visible wavelengths and for most materials. The diffractive portion may be any surface that diffracts light and includes holographic kinoforms, phase Fresnel lenses, phase plates, binary gratings and surfaces made with binary optics. The diffractive portion and the positive lens system are monofocal.

The positive lens system may include one or more lenses so long as the system is positive, i.e., directs or converges light toward the negative IOL portion. If only one diffractive surface portion is provided, it is preferred to provide it on a surface of the lens system and preferably on the entry element of the lens system.

Another advantage of the invention is that the positive lens system may include only a single lens or refracting element having a magnifying power other than unity. This reduces the size and weight of the lens system as compared with multi-element external lens systems thereby increasing patient comfort. In addition, even though a single external lens is employed, a relatively high magnification, e.g. 4× or more, can be obtained while maintaining a relatively small vertex distance. This can all be accomplished while correcting in whole or in part for chromatic, spherical, and/or other optical aberrations utilizing only a single external lens.

When only a single positive lens is employed in the positive lens system, the diffractive portion may be on either the front or back surface of that lens. However, preferably, it is on the back surface. The diffractive portion may compensate for chromatic aberrations of the positive lens and/or for all of the lenses of the ophthalmic lens system. Alternatively, a lens surface of the IOL may include a diffractive portion to correct for the chromatic aberrations of the IOL.

Another feature of the invention is that, at least a first of the lens surfaces of the ophthalmic lens system is aspheric, and this may be used to correct for optical aberrations such as spherical, comatic, field curvature, astigmatism, etc. in the image, rather than to obtain a multifocal power. Although any one or more lens surfaces of the ophthalmic lens system may be aspheric, preferably, a lens of the positive lens system is aspheric. Alternatively, one surface of the IOL may be aspheric. The aspheric surface may correct for the optical aberrations of the lens on which it is located or for the optical aberrations of the entire ophthalmic lens system.

In a preferred system, a single positive lens has an aspheric front surface and a diffractive back surface. If desired, the diffractive surface and the aspheric surface may be the same surface. The diffractive surface adds power to reduce the thickness and weight of the lens.

The positive lens system is external to the eye, and although it may be or include a contact lens, preferably the positive lens system is mounted on a spectacle frame. The thinness and light weight of the positive lens adapts it for attachment to a clip-on or add-on spectacle frame over regular spectacles. Although the spectacle frame may be of various different kinds, and may, if desired, not permit relative movement between the positive lens and the frame, preferably the spectacle frame mounts the lens for movement generally along the optical axis of the lens.

BRIEF DESCRIPTION OF THE DRAWINGS

FIG. 1 is a schematic illustration of an ophthalmic lens system.

FIG. 2 is a schematic view similar to FIG. 1 with the external lens removed.

FIG. 3 is an elevational view of one form of IOL that can be used in the ophthalmic lens system of FIG. 1.

FIG. 4 is an enlarged fragmentary view illustrating one preferred form of the diffractive surface.

FIG. 5 is a perspective view illustrating spectacles which include two of the positive lenses of the ophthalmic lens system.

FIG. 6 is an exploded perspective view illustrating a preferred way in which the spectacle frame mounts an associated positive lens for axial movement.

FIG. 7 is an axial sectional view through a lens holding assembly for mounting one of the external lenses.

DESCRIPTION OF THE PREFERRED EMBODIMENT

FIG. 1 shows an ophthalmic lens system 11 which generally comprises a positive lens system, including only a single, monofocal positive lens 13, and an IOL 15 implanted the eye of a patient. FIG. 1 also illustrates the cornea 17, and retina 21 of the patient.

Light entering the positive lens 13 from an object (not shown) is converged and directed by the lens 13 toward a central negative lens portion 22 of the IOL 15. The negative lens portion 22 of the IOL 15 directs the light onto the retina 21. The cornea 17 also serves as a positive lens, but this can be ignored in the discussion of the ophthalmic lens system 11.

The positive lens 13 is an external lens in that it is located outside of the eye. The lens 13 has a front lens surface 23 and a back lens surface 25.

The IOL 15 includes an optic 27 (FIG. 3) and fixation members 29 for fixing the IOL within the eye of a patient. The IOL 15 may be of various different kinds and constructions, provided that it has a negative lens portion. In the specific embodiment illustrated, the optic 27 includes the central negative lens portion 22 and an annular positive lens portion 26. In this embodiment, the negative lens portion 22 is biconcave and the positive lens portion 26 is biconvex; however, these configurations are merely illustrative. The negative lens portion 22 has a front lens surface 33 and a back lens surface 35. The fixation members 29 may be of different kinds and constructions.

The positive lens 13 and the IOL 15 are centered on an optical axis 36. The IOL 15 may be implanted at any of the desired locations within the eye, such as the anterior chamber or the posterior chamber.

Any one of the lens surfaces 23, 25, 33 and 35 or any combination of these lens surfaces may include a diffractive portion in the embodiment of FIG. 1, only the back lens surface 25 of the positive lens 13 has a diffractive portion. More specifically, the entire back lens surface 25 is diffractive. In this embodiment, the diffractive portion of the back lens surface 25 has sufficient power to correct for the chromatic aberrations of the positive lens 13.

As another example, one of the lens surfaces 23 and 25 of the positive lens 13 and one of the lens surfaces 33 and 35 of the negative IOL lens portion 22 have diffractive portions. Although any of the lens surfaces 23, 25, 33 and 35 may be diffractive, ordinarily no more than one diffractive lens surface per lens element is desired.

Although the diffractive surface may be of various different kinds, in this embodiment, it may be of the type having a linear blaze profile which can theoretically direct nearly all of the incident light into a focus. This profile, which is shown somewhat schematically and not to scale in FIG. 4, comprises a large number of very small annular, coaxial steps 34 each defined by an axial cylindrical surface 38 and a sloping annular surface 40 which intersects the associated axial surface 38. FIG. 4 greatly exaggerates the axial dimension of the cylindrical surfaces 38 relative to the radial spacing between the cylindrical surface.

Preferably any one or more of the lens surfaces 23, 25, 33 and 35 is aspheric to correct in whole or in part for one or more optical aberrations such as spherical, comatic, field curvature, astigmatism, etc. of the associated lens or of the entire lens system 11. The aspheric surface or surfaces may be the same as, or different from, the surface or surfaces which are diffractive. Ordinarily no more than one aspheric lens surface per lens element is desired. An aspheric surface on an ophthalmic lens is described for example in Burk U.S. Pat. No. 4,504,982 and Mercier U.S. Pat. No. 4,957,506. In one example, the diffractive surface and the aspheric surface are the same surface, such as any one of the surfaces 23, 25, 33 and 35.

The front lens surface 23 of the positive lens 13 is convex, and the back lens surface 25 is slightly convex. Preferably, the front lens surface 23 is aspheric to correct in whole or in part for one or more optical aberrations. In this embodiment, the asphericity of the positive lens 13 is sufficient to correct in whole or in part for one or more optical aberrations of the positive lens 13. As another example, one of the lens surfaces 33 and 35 of the negative IOL lens portion 22 may be aspheric to correct in whole or in part for the one or more optical aberrations of that lens.

The positive lens 13 will typically have fairly high diopter power and may be, for example, in the range of +20 diopters to +30 diopters. Typically, the front lens surface 33, which is a refractive surface, will provide most of this power, and the diffractive portion on the back lens surface 25 will provide only enough power to correct for chromatic aberrations of the lens 13. For example, the refractive front lens surface 23 may provide about 24 diopters with a posterior lens refractive surface 25 providing about 2 diopters for a total "refractive" power of about 26 diopters, and the back diffractive lens surface 25 may provide about 2 to 3 diopters. Thus the refractive and diffractive portions of the lens 13 cooperate to direct and converge light toward the negative lens portion 22. A similar relationship would exist if the IOL 15 were provided with a diffractive surface portion.

The positive lens 13 can be constructed of known lens materials with polymeric materials being preferred. For example, polycarbonate or polymethylmethracylate (PMMA) can be employed.

The negative lens portion 22 of the IOL 15 typically has a high negative power which may range, for example, from about −40 diopters to about −100 diopters. Either or neither of the lens surfaces 33 and 35 may be aspheric to correct in whole or in part for one or more optical aberrations of the IOL 15, and either or neither of these lens surfaces may have a diffractive portion to correct for chromatic aberrations of the IOL. The positive lens portion may have, for example, a power from about 10 diopters to about 35 diopters. The IOL may be constructed of any suitable IOL materials, including, for example, PMMA, glass, silicone or acrylics. The IOL is may be either rigid or foldable.

The ophthalmic lens system 11 is designed for use in a single eye of a patient. A similar ophthalmic lens system 11 would be used for the other eye.

The positive lens 13 may be any lens which is external to the eye. Although it may be a contact lens, preferably, it is a spectacle lens. In that regard, FIG. 5 shows spectacles 37 which comprise a spectacle frame 39 and two of the positive lenses 13 mounted on the spectacle frame 39.

With the spectacles 37 being worn, light is directed toward the negative IOL portion 22 by the positive lens 13 and light is directed toward the retina 21 as shown in FIG. 1 to achieve the desired high magnification with a relatively small vertex distance and with both chromatic and optical aberration correction. With the spectacles removed as shown in FIG. 2, the positive IOL lens portion 26 functions in the conventional manner for IOL's by focusing light at the retina 21.

The spectacle frame 39 may be of various different kinds and may, if desired, fixedly mount the positive lenses 13 so they are immovable relative to the spectacle frame. However, preferably the positive lenses 13 are mounted on the spectacle frame so that they can move along the optical axis 36 relative to the spectacle frame. By moving the positive lenses 13 along the optical axis 36 relative to the IOL's 15, enhanced visual acuity at various different focal lengths can be provided.

Various different techniques and constructions may be employed to mount the positive lenses 13 for movement along the optical axis 36. One preferred system is shown in FIGS. 5–7. This construction is similar to that shown and described in common assignee's copending U.S. application Ser. No. 788,478 filed on Nov. 6, 1991.

As shown in FIGS. 5–7, the spectacle frame 37 includes two identical lens holding assemblies 42, one for each of the positive lenses 13. Each of the assemblies 42 includes a tubular housing member 41 of a rigid polymeric material having a cylindrical passage 43 and a flange 45 which is suitably retained within a lens holding ring 47 of the spectacle frame. A tubular lens holder 49 is slidably received within the passage 43 as shown in FIG. 7 and has a passage 51 with an internal annular shoulder 53. The positive lens 13 is received within the passage 51 of the lens holder 49 and is retained against the shoulder 53 by a retaining ring 55 which may be, for example, adhesively retained within the passage 51. Alternatively, the retaining ring 55 may be a conventional split ring which is receivable within a groove (not shown) of the lens holder 49.

The lens holder 49 has an L-shaped slot 57 which includes an axial portion 59 opening at one edge of the lens holder and a circumferential portion 61. The housing member 41 has an axial slot 63 that opens at one edge of the housing member.

As shown in FIG. 7, the circumferential portion 61 of the L-shaped slot 57 is aligned with the slot 63 of the housing member and a driver 65 projects into the slot 63 and the circumferential portion 61. The slot 63 is displaced circumferentially from the axial portion 59 of the slot 57. The driver 65 is one component of a mechanism which provides for non-rotational and translational movement of the lens holder 49 along the optical axis 36 in order to adjust the axial distance between the positive lens 13 and the associated IOL 15 (FIG. 1). A rotatable actuator 67 cooperates with the driver 65 to move the positive lens 13 along the optical axis 36.

A housing 69, which includes housing sections 71 and 73 is attached to the housing member 41 in any suitable manner such as by screws 75. The housing sections 71 and 73 may be releasably joined as by screws 77.

The actuator 67 includes a threaded portion 79 which is received within and cooperates with a threaded hole or saddle 81 in the driver 65. A dowel 83, which is mounted on the housing sections 71 and 73 and which extends through an opening 85 in the driver 65, assists in mounting the driver 65 for translating movement. The lens holder 49 is adequately held against rotation by friction. Rotational support for the actuator 67 includes a shaped cavity 87 in the housing section 73 and the threaded engagement between the threaded portion 79 and the threads in the hole 81 of the driver 65.

More specifically, the actuator 67 includes a knurled wheel 89 and a portion 91 of this wheel projects outwardly of the cavity 87 to enable it to be manually rotated. Manual rotation of the wheel 89 urges the driver 65 axially in the slot 63 to drive the lens holder 49 and the positive lens 13 along the optical axis 36 without rotating the lens or the lens holder. Of course, counter rotating the actuator 67 moves the lens holder 49 and the positive lens 13 in the opposite direction along the optical axis 36.

A specific example, which is set forth purely by way of illustration and not by way of limitation, of the lens 13 and the IOL 15 is set forth below. In this example, the positive lens 13 is constructed of PMMA, has a diameter of 34 mm and a thickness along the optical axis 36 between the front lens surface 23 and the back lens surface 25 of 10.534 mm. The diameter of the IOL 15 is 6 mm and the diameter of the negative IOL portion is 2 mm. The thickness of the IOL 15 along the optical axis 36 is 0.3 mm.

The front surface 23 of the positive lens 13 is an aspheric surface of revolution about the optical axis 36 and is defined by the aspheric equation for a radial plane through the optical axis 36 as follows:

$$z = \frac{py^2}{1 + (1 - (1 + K) p^2 y^2)^{\frac{1}{2}}} + Ay^4 + By^6 + Cy^8 + Dy^{10}$$

where p is the curvature at the vertex

K is a conic constant

A, B, C, D are aspheric coefficients z is the distance along the optical axis 36 y is the coordinate of distance perpendicular to optical axis

Utilizing the aspheric equation, the parameters for the front lens surface 23 and the back lens surface 25 of the positive lens 13 and the front lens surface 33 and the back lens 35 of the IOL 15 are shown in the table below. In this table, the first six parameters are for the front lens surface and the second six parameters are for the back lens surface.

| Parameter (Units) | Lens 13 | Negative IOL Lens Portion 22 |
|---|---|---|
| $p$ (mm$^{-1}$) | 0.04878848 | −0.22396417 |
| k | 0 | 0 |
| A (mm$^{-3}$) | −2.14326 × 10$^{-6}$ | −1.10574 × 10$^{-3}$ |
| B (mm$^{-5}$) | −1.85095 × 10$^{-8}$ | 2.50560 × 10$^{-2}$ |
| C (mm$^{-7}$) | −8.12792 × 10$^{-11}$ | −2.95500 × 10$^{-2}$ |
| D (mm$^{-9}$) | 0 | 1.22390 × 10$^{-2}$ |

-continued

| Parameter (Units) | Lens 13 | Negative IOL Lens Portion 22 |
|---|---|---|
| p (mm$^{-1}$) | $-4.13826 \times 10^{-3}$ | 0.31948882 |
| k | 0 | 0 |
| A (mm$^{-3}$) | 0 | 0 |
| B (mm$^{-5}$) | 0 | 0 |
| C (mm$^{-7}$) | 0 | 0 |
| D (mm$^{-9}$) | 0 | 0 |

The back lens surface 25 is diffractive and is defined by the parameters given above in the table plus a phase function. The phase function is a sum of monomials in (x,y) with the coordinates on the back lens surface 25. The phase function gives the amount of phase variation across the back lens surface 25 and defines the spacing of the diffractive steps, i.e. the radial spacing between the cylindrical surfaces 38. The axial dimension of the cylindrical surfaces 38 for a PMMA lens 13 used in air is about 1.1 micron.

The phase function, Qxy, is set forth in the following phase function equation:

$$Q_{xy} = ax^2 + by^2 + cx^4 + dx^2y^2 + ey^4 + fy^6 + gx^4y^2 + hx^2y^4 + iy^6 + jy^8 + kx^6y^2 + lx^4y^4 + mx^2y^6 + ny^8$$

where a, b, c, d, e, f, g, h, i, j, k, l, m, n are coefficients and x, y are in millimeters. For a circularly symmetric function about the optical axis
 a=b
 c=e=d/2
 f=i
 j=n=l/6
 g=h=3f=3i
 k=m=4j=4n The coefficients are:
 a=b=$0.144470 \times 10^{-2}$ mm$^{-1}$
 c=e=$-0.706813 \times 10^{-5}$ mm$^{-3}$
 f=i=$0.329517 \times 10^{-7}$ mm$^{-5}$
 g=h=$0.988550 \times 10^{-7}$ mm$^{-5}$
 j=n=$-0.560201 \times 10^{-10}$ mm$^{-7}$
 k=m=$-0.224080 \times 10^{-9}$ mm$^{-7}$
 d=$-0.141363 \times 10^{-4}$ mm$^{-3}$
 l=$-0.336120 \times 10^{-9}$ mm$^{-7}$ If the phase function is evaluated only in a radial plane extending through the optical axis 36, the function is:

$$Q_{xy} = by^2 + ey^4 + fy^6 + jy^8 \text{ (at } x=0\text{)}$$

The positive IOL lens portion can also be defined using the aspheric equation set forth above. For the front or anterior surface of the lens portion 26, p=0.0829170 mm$^{-1}$, and for the back or posterior surface of the positive IOL lens portion 26, p=$-3.90198 \times 10^{-2}$ mm$^1$. The coefficients K, A, B, C, and D are zero.

Although exemplary embodiments of the invention have been shown and described, many changes, modifications and substitutions may be made by one having ordinary skill in the art without necessarily departing from the spirit and scope of this invention.

We claim:

1. An ophthalmic lens system comprising:
   an intraocular lens adapted for implantation in an eye and having a negative intraocular lens portion;
   a positive lens system adapted to be outside the eye and direct light toward the negative intraocular lens portion of the intraocular lens;
   each of the intraocular lens portion and the positive lens system having a plurality of lens surfaces; and
   at least one of said lens surfaces including a diffractive portion for at least partially correcting for chromatic aberrations.

2. A system as defined in claim 1 wherein at least a first of said lens surfaces is aspheric.

3. A system as defined in claim 1 wherein said one lens surface is on the positive lens system and at least one of said lens surfaces of the negative intraocular lens portion includes a diffractive portion.

4. A system as defined in claim 1 wherein at least a first of the lens surfaces of the positive lens system is aspheric to correct in whole or in part for one or more optical aberrations.

5. A system as defined in claim 4 wherein at least a first of the lens surfaces of the intraocular lens portion is aspheric to correct in whole or in part for one or more optical aberrations.

6. A system as defined in claim 1 including a spectacle frame and the positive lens system is mounted on the spectacle frame.

7. A system as defined in claim 1 wherein the positive lens system includes an ophthalmic lens with a positive ophthalmic lens portion and said lens surfaces include back and front surfaces of the intraocular lens portion and the ophthalmic lens portion and said one lens surface includes one of said front and back surfaces.

8. A system as defined in claim 7 wherein said one lens surface is one of the back and front surface of the positive ophthalmic lens portion.

9. A system as defined in claim 7 wherein said one lens surface is the back surface of the positive ophthalmic lens portion.

10. A system as defined in claim 7 wherein a first of the back and front surfaces of the positive ophthalmic lens portion is an aspheric surface.

11. A system as defined in claim 10 wherein said first surface is said front surface of the positive ophthalmic lens portion and said one surface is the back surface of the positive ophthalmic lens portion.

12. A system as defined in claim 7 wherein said positive ophthalmic lens portion is the only refracting element of the positive lens system which has a magnifying power other than unity.

13. An ophthalmic lens system comprising:
   an intraocular lens adapted for implantation in the eye and having a negative intraocular lens portion;
   spectacles including a positive lens adapted to direct light toward the negative intraocular lens portion of the intraocular lens, said positive lens having front and back surfaces; and
   at least one of said surfaces including a diffractive portion.

14. A system as defined in claim 13 wherein said one surface is the back surface of the positive lens.

15. A system as defined in claim 13 wherein at least a first of said surfaces is aspheric.

16. A system as defined in claim 13 wherein said one surface is the back surface of the positive lens and the front surface of the positive lens is aspheric.

17. A system as defined in claim 16 wherein the of the diffractive portion provides a correction for chromatic aberration and the aspheric front surface of the positive lens has a power which is larger than the power of the diffractive portion.

18. A system as defined in claim 13 wherein the power of the positive lens is at least about 20 diopters and the negative power of the intraocular lens is about −40 diopters or more negative.

19. A system as defined in claim 13 wherein said positive ophthalmic lens portion is the only refracting element of the positive lens system which has a magnifying power other than unity.

20. A system as defined in claim 15 wherein said one surface and said first surface are the same surface.

21. A method of correcting for macular degeneration comprising passing light through a positive lens system located outside an eye and having a diffractive surface and then through a negative intraocular lens portion located within the eye.

22. An ophthalmic lens system for assisting patients with central retinal visions problems comprising:

an intraocular lens adapted for implantation in the eye and having a negative intraocular lens portion;

spectacles including a monofocal positive lens adapted to direct light toward the negative intraocular lens portion of the intraocular lens, said positive lens having front and back surfaces; and at least one of said surfaces including a diffractive portion for at least partially correcting for chromatic aberrations.

23. A system as defined in claim 22 wherein at least one of said surfaces is aspheric to at least partially correct for one or more optical aberrations, said aspheric surface and said diffractive surface cooperating to direct light toward the negative intraocular lens portion.

* * * * *